(12) United States Patent
Metrani

(10) Patent No.: US 10,018,506 B2
(45) Date of Patent: Jul. 10, 2018

(54) MULTIFUNCTIONAL INFRARED MODULE

(71) Applicant: Peel Technologies, Inc., Mountain View, CA (US)

(72) Inventor: Samyeer Suresh Metrani, Milpitas, CA (US)

(73) Assignee: Peel Technologies, Inc., Mountain View, CA (US)

( * ) Notice: Subject to any disclaimer, the term of this patent is extended or adjusted under 35 U.S.C. 154(b) by 0 days.

(21) Appl. No.: 15/475,087

(22) Filed: Mar. 30, 2017

(65) Prior Publication Data

US 2017/0284865 A1    Oct. 5, 2017

Related U.S. Application Data

(60) Provisional application No. 62/315,636, filed on Mar. 30, 2016.

(51) Int. Cl.
*G01J 5/20*    (2006.01)
*G01J 1/44*    (2006.01)
*G01J 1/02*    (2006.01)

(52) U.S. Cl.
CPC .............. *G01J 1/44* (2013.01); *G01J 1/0295* (2013.01); *G01J 2001/446* (2013.01); *G01J 2001/4473* (2013.01)

(58) Field of Classification Search
CPC .... G01J 5/20; G01J 5/08; H01L 31/09; H01L 27/14649; H04N 5/33
See application file for complete search history.

(56) References Cited

U.S. PATENT DOCUMENTS

| | | | | |
|---|---|---|---|---|
| 3,648,073 | A | * | 3/1972 | Sams ................. H03K 5/02 327/111 |
| 4,258,719 | A | * | 3/1981 | Lewyn ............ A61B 5/02416 307/650 |
| 4,907,594 | A | | 3/1990 | Muz |
| 5,075,792 | A | * | 12/1991 | Brown .................. H04B 10/40 341/69 |

(Continued)

OTHER PUBLICATIONS

PCT International Search Report and Written Opinion, PCT Application No. PCT/US2017/025203, dated Jun. 9, 2017, 12 pages.

*Primary Examiner* — David Porta
*Assistant Examiner* — Mamadou Faye
(74) *Attorney, Agent, or Firm* — Fenwick & West LLP

(57) ABSTRACT

A multifunctional infrared (IR) module is configured for multiple IR applications without an additional microcontroller to be integrated into a computing device and is able to utilize voltage control instead of current control. The multifunctional IR module includes an IR light emitting diode (LED), and an IR receiver (e.g., photodiode or phototransistor). In one embodiment, the multifunctional IR module includes a resistor that is connected to the cathode of the IR LED and the drain of a transistor, with the source of the transistor grounded. In some embodiments, the multifunctional IR module additionally includes a red LED. Various configurations of the multifunctional IR module are able to perform one or more of the following functions: IR in (receiving IR signals), IR out (generating IR signals), heart rate sensing, SpO$_2$ (oxygen saturation) sensing, distance/proximity detection, gesture detection, LED control, and ambient light detection.

17 Claims, 6 Drawing Sheets

(56) References Cited

U.S. PATENT DOCUMENTS

| | | | | |
|---|---|---|---|---|
| 2005/0127297 A1* | 6/2005 | Starta | ................. | G01N 21/3504 250/341.5 |
| 2009/0146992 A1* | 6/2009 | Fukunaga | ........... | G02F 1/13338 345/214 |
| 2010/0324384 A1* | 12/2010 | Moon | .................... | A61B 5/746 600/323 |

* cited by examiner

MULTIFUNCTIONAL INFRARED MODULE

CROSS-REFERENCE TO RELATED APPLICATIONS

This application claims the benefit of U.S. Provisional Patent Application No. 62/315,636, filed on Mar. 30, 2016, which is hereby incorporated by reference.

BACKGROUND

This application relates generally to infrared technologies, and in particular to a hardware module configured for multiple infrared applications.

Infrared (IR) technology has many useful applications, including measuring heart rate, measuring SpO2, measuring distance, and communicating (i.e., generating and receiving) signals used to transmit information. Because they involve sending and/or receiving IR signals, these seemingly disparate applications require the same basic components—an IR light-emitting diode (LED) and an IR receiver. However, those two components alone are conventionally not enough to fully implement the techniques used for those applications, and integrating IR technology into computing devices can be costly and can increase power consumption due to the additional hardware required.

BRIEF DESCRIPTION OF DRAWINGS

The disclosed embodiments have other advantages and features which will be more readily apparent from the detailed description, the appended claims, and the accompanying figures. A brief introduction of the figures is below.

DETAILED DESCRIPTION

Figure 1:
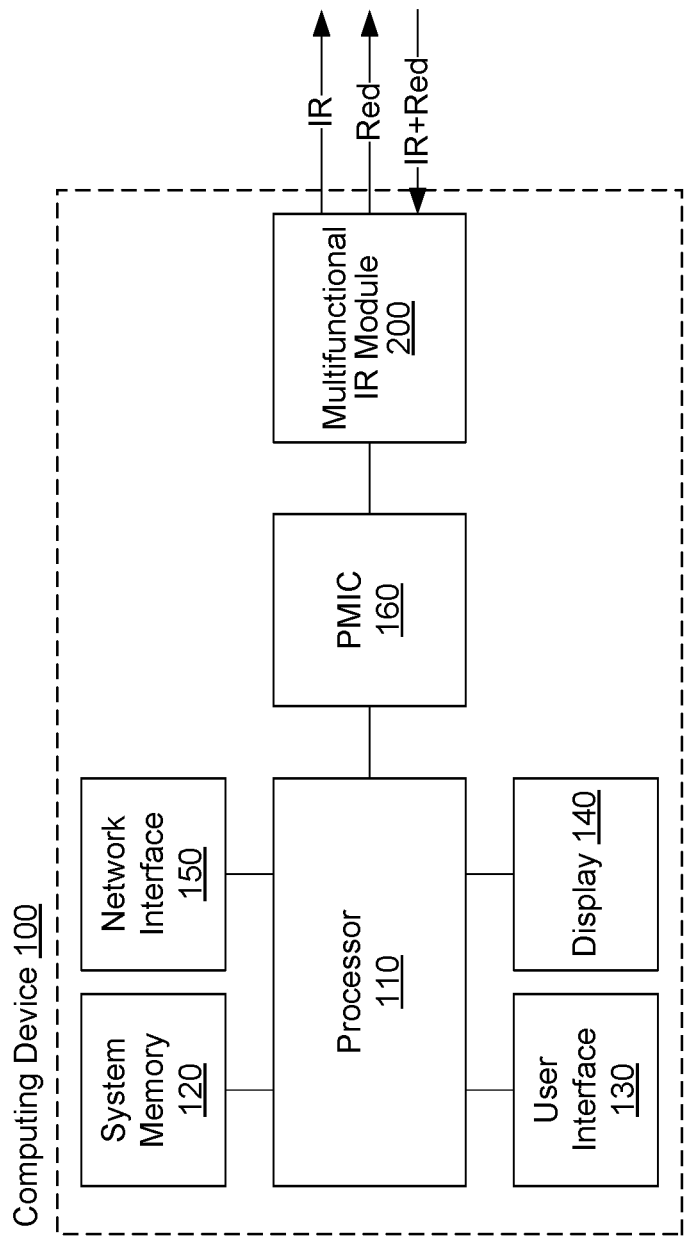
FIG. 1 is a block diagram a computing device with a multifunctional infrared (IR) module, according to one embodiment.

The Figures (FIGS.) and the following description relate to preferred embodiments by way of illustration only. It should be noted that from the following discussion, alternative embodiments of the structures and methods disclosed herein will be readily recognized as viable alternatives that may be employed without departing from the principles of what is claimed.

Reference will now be made in detail to several embodiments, examples of which are illustrated in the accompanying figures. It is noted that wherever practicable similar or like reference numbers may be used in the figures and may indicate similar or like functionality. The figures depict embodiments of the disclosed system (or method) for purposes of illustration only. One skilled in the art will readily recognize from the following description that alternative embodiments of the structures and methods illustrated herein may be employed without departing from the principles described herein.

Overview

A multifunctional infrared (IR) module is configured for multiple IR applications with minimal additional hardware. Specifically, it does not require an additional microcontroller to be integrated into a computing device and is able to utilize voltage control instead of current control. The multifunctional IR module includes an IR light emitting diode (LED), and an IR photodiode. In some embodiments, it additionally includes a red LED. Various configurations of the multifunctional IR module are able to perform one or more of the following functions: IR in (receiving IR signals), IR out (generating IR signals), heart rate sensing, $SpO_2$ (oxygen saturation) sensing, distance/proximity detection, gesture detection, LED control, and ambient light detection.

Example Computing Machine Architecture

Figure (FIG.) 1 is a block diagram of a computing device a multifunctional infrared (IR) module, according to one embodiment. The computing device 100 may be a personal computer (PC), a tablet, a personal digital assistant (PDA), a smartphone, an electronic device (e.g., a television, a stereo, etc.), or any other machine capable of generating and/or receiving an infrared signal. Furthermore, while only a single computing device 100 is illustrated, the term "computing device" shall also be taken to include any collection of devices that individually or jointly perform any one or more of the methodologies discussed herein.

The example computing device 100 includes one or more processors 110 (e.g., a central processing unit (CPU), a digital signal processor (DSP), one or more application specific integrated circuits (ASICs), or any combination of these) and a system memory 120 (e.g., a hard disk, an optical drive, a solid state drive, or any combination of these). The system memory 120 includes a machine-readable medium storing instructions (e.g., software) or program code embodying any one or more of the methodologies or functions described herein. Furthermore, the system memory 120 may also include volatile memory. The instructions or program code may also reside, at least partially, within the processor 110 (e.g., within a processor's cache memory) during execution thereof.

While the machine-readable medium is shown in an example embodiment to be a single medium, the term "machine-readable medium" should be taken to include a single medium or multiple media (e.g., a centralized or distributed database, or associated caches and servers) able to store instructions. The term "machine-readable medium" shall also be taken to include any medium that is capable of storing instructions or program code for execution by the machine and that cause the machine to perform any one or more of the methodologies disclosed herein. The term "machine-readable medium" includes, but not be limited to, data repositories in the form of solid-state memories, optical media, and magnetic media.

The instructions may be transmitted over a network via a network interface 150 connected to the processor 110. The network interface 150 operatively connects the computing device 100 to one or more networks. For example, the network interface 150 may connect the computing device 100 to a wired or wireless network using technologies such as Ethernet, 802.11, worldwide interoperability for microwave access (WiMAX), 3G, 4G, Long Term Evolution (LTE), code division multiple access (CDMA), digital subscriber line (DSL), BLUETOOTH™, etc. Examples of networking protocols used include multiprotocol label switching (MPLS), transmission control protocol/Internet protocol (TCP/IP), hypertext transport protocol (HTTP), simple mail transfer protocol (SMTP), and file transfer protocol (FTP). In some embodiments, some or all of the data is encrypted using any suitable technique or techniques.

The computer system 100 may further include an input device 130 (e.g., a keyboard, a touchscreen, a keypad, a joystick, etc.) and a display 140 (e.g., a plasma display panel (PDP), a liquid crystal display (LCD), a projector, or a cathode ray tube (CRT)) to receive and output data to a user, respectively. In some embodiments, a single component, such as a touchscreen, may be configured as both an input device 130 and a display 140.

The computing device 100 includes a power management integrated circuit (PMIC) 160. The PMIC 160 controls, regulates and distributes power in the computing device 100. The PMIC 160 may aim to minimize power consumption, especially if the computing device 100 is battery-powered. The PMIC 160 can include one or more of an alternating current-to-direct current (AC-to-DC) converter, a DC-to-DC converter, an analog-to-digital converter (ADC), a digital-to-analog converter (DAC), and a low-dropout (LDO) regulator. The PMIC 160 may also support pulse-frequency modulation (PFM), and pulse-width modulation (PWM), as well as general-purpose input-output (GPIO), inter-integrated circuit (I2C), and serial peripheral interface (SPI) configurations. In addition, the PMIC 160 can drive particular modules, such as a multifunctional IR module 200, based on instructions from the processor 110. The PMIC 160 is shown as being only connected to the multifunctional IR module 200 in FIG. 1, though in reality the PMIC 160 may be connected to many or all of the aspects of the computing device 100 that require power.

In some embodiments, the multifunctional IR module 200 is directly connected to the processor 110 in addition to being connected to the PMIC 160. The PMIC 160 may provide the voltage inputs to the multifunctional IR module 200, and either the PMIC 160 or the processor 110 may provide GPIO and/or PWM outputs. Additionally, though most ADCs are part of the PMIC 160, in some embodiments, the ADC may be provided by the processor 110. Alternatively, in some embodiments the PMIC 160 is part of the processor 110 and the multifunctional IR module 200 is indirectly connected to the PMIC 160 through the processor 110.

The computing device 100 further includes the multifunctional IR module 200. In some embodiments, the multifunctional IR module 200 is not physically a part of the computing device 100 and may instead be a separate unit connected to the computing device 100, such as a dongle. The multifunctional IR module 200 is a component or set of components capable of emitting IR and red light, and, in some embodiments, receiving IR light. IR light refers to the portion of the electromagnetic spectrum having wavelengths from ~750 nm to ~1500 nm. Red light refers to portion of the electromagnetic spectrum having wavelengths from ~620 nm to ~750 nm. The multifunctional IR module 200 includes an IR light-emitting diode (LED; IR LED can also be shortened to IRED for IR-emitting diode), a photodiode, and a red LED (can also be shortened to RED for red-emitting diode). The photodiode may detect all or a portion of the entire visible and IR spectrum. For example, the photodiode may detect light from ~400 nm to 1100 nm. In some embodiments, the IR and red LEDs are replaced by other types of light emitters, or LEDs of different colors, such as a green LED. Similarly, in some embodiments, the photodiode is replaced by another type of photodetector, such as for example, a photoresistor, a phototransistor, or a reverse-biased LED. In one embodiment, the IR LED is capable of emitting and detecting IR light. In some embodiments, the multifunctional IR module 200 does not include a red LED.

In some cases, the IR signal generated by the multifunctional IR module 200 is received by an external device. The external device may be an electronic device such as a television, a stereo, a computer, or a home appliance. Examples of a home appliance include a heater, a fan, a thermostat, a garage door, or an air conditioner. The external device can be any other applicable device that receives commands via IR signals. For example, the external device may be a set-top box, a digital video recorder (DVR), a video player (including but not limited to a Blu-ray player, a DVD player, a VCR player, and the like), a gaming console, a digital media player (including but not limited to an APPLE TV, a ROKU BOX, and the like), a sound system, a camera, or an IR-enabled toy. These example embodiments of an external device may be connected to a television or implemented as standalone devices. Additionally or alternatively, the multifunctional IR module 200 may be configured to receive an IR signal generated by one or more external devices or transmit an IR signal to one or more external devices. For example, the computing device 100 communicates with a television via IR signals to adjust the volume of the television, but may communicate with a set-top box via IR signals to select the channel playing on the television.

Example Multifunctional IR Module

Figure 2:
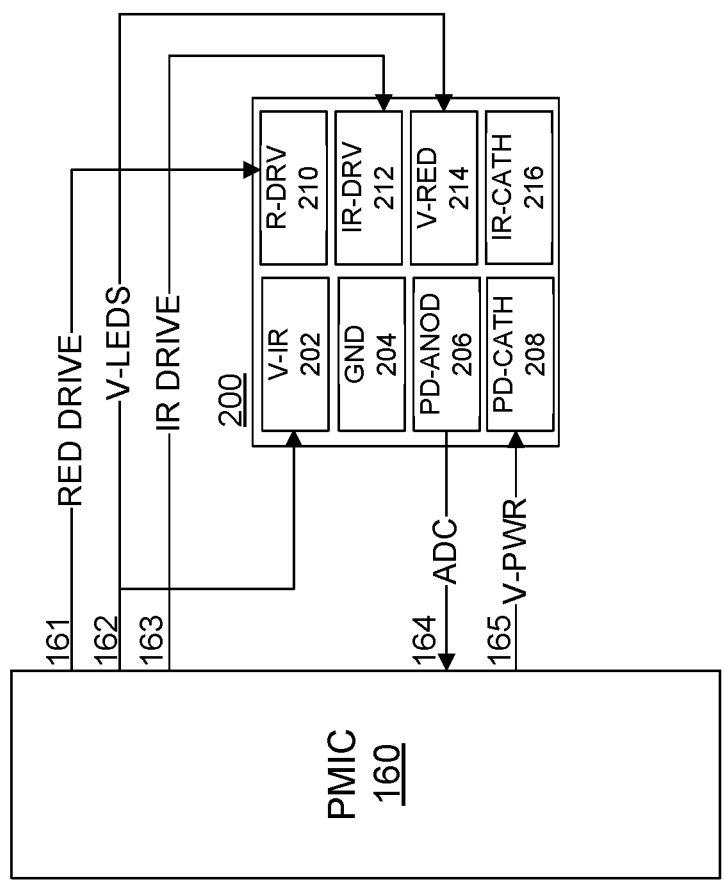
FIG. 2 illustrates a multifunctional IR module connected to a power management integrated circuit of a computing device, according to one embodiment.

FIG. 2 illustrates the multifunctional IR module 200 connected to the PMIC 160 of the computing device 100, according to one embodiment. The multifunctional IR module 200 has eight pins 202-216. $V_{IR}$ pin 202 powers the IR LED. GND pin 204 is the ground. The anode of photodiode is $PD_{ANOD}$ pin 206, and the cathode of photodiode is $PD_{CATH}$ pin 208. RDRV pin 210 drives the red LED. $IR_{DRV}$ pin 212 drives the IR LED. $V_{RED}$ pin 214 powers the red LED. $IR_{CATH}$ pin 216 is the cathode of the IR LED.

The multifunctional IR module 200 receives four signals 161-165 from the PMIC 160. Signal 161 connects to $R_{DRV}$ pin 210 and drives the red LED. In some embodiments, signal 161 is a PWN-GPIO led control, while in other embodiments it is a SPI MOSI led control. Signal 162 powers both $V_{IR}$ pin 202 and $V_{RED}$ pin 214. In some embodiments, signal 162 is 200 mA current. Signal 163 connects to $IR_{DRV}$ pin 212 and drives the IR LED. In some embodiments, signal 163 is a PWM-GPIO led control, while in other embodiments it is a SPI MOSI led control. Additionally, multifunctional IR module 200 sends one signal to the PMIC 160. Signal 164 is the output from the anode of photodiode 240 via the $PD_{ANOD}$ pin 206. Signal 165 powers the $PD_{CATH}$ pin 208. In some configurations, such as that shown in FIG. 5, signal 165 is not used, and signal 164 is output from the cathode of the photodiode 240 via the $PD_{CATH}$ pin 208.

Figure 3:
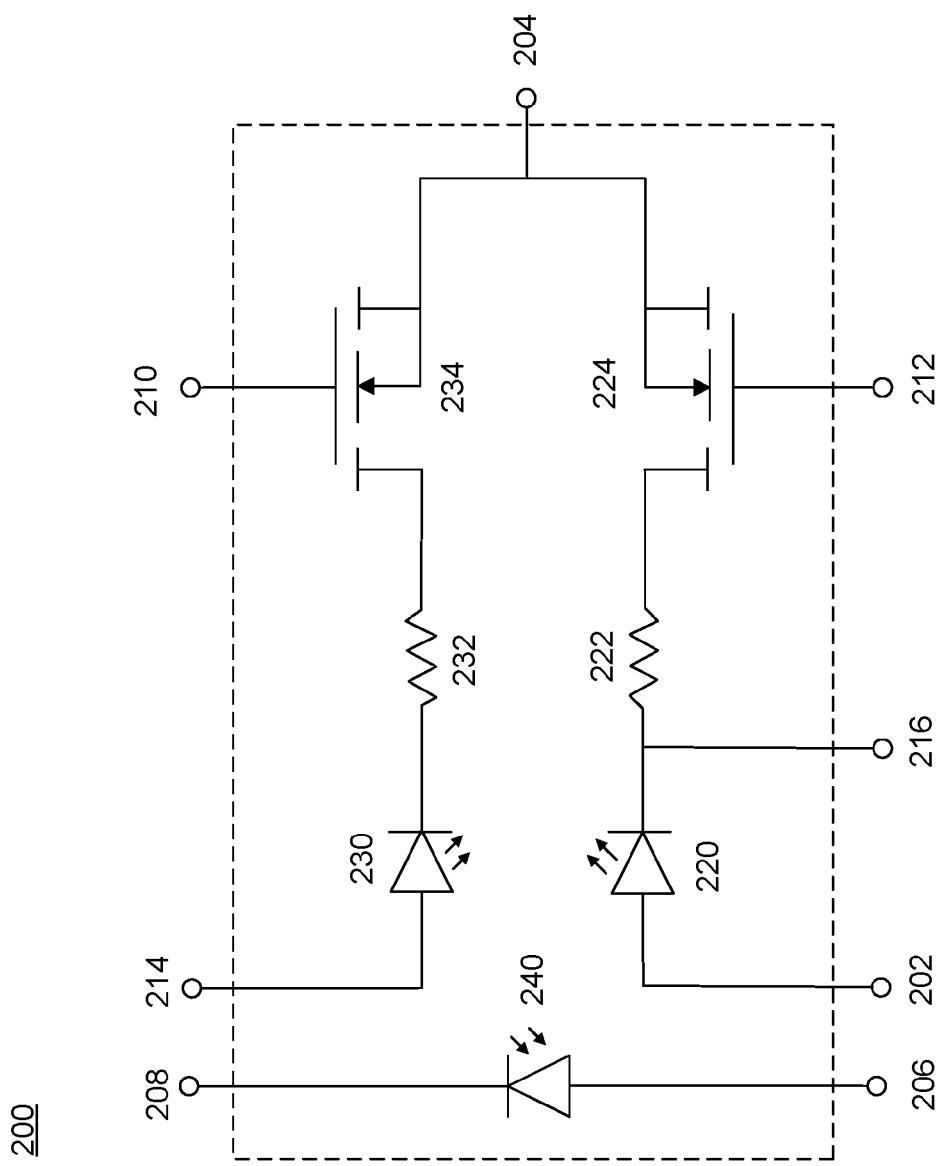
FIG. 3 illustrates circuitry of a multifunctional IR module, according to one embodiment.

FIG. 3 illustrates circuitry of a multifunctional IR module 200, according to one embodiment. The primary components of the multifunctional IR module 200 are IR LED 220, red LED 230, and photodiode 240. The circuitry of the multifunctional IR module 200 also includes two resistors 222 and 232, and two transistors 224 and 234 to form driving circuits for the IR LED 220 and red LED 230. The transistors 224 and 234 may be N field effect transistors (N-FETs). Resistor 222 and transistor 224 may form the driving circuit for IR LED 220. Resistor 232 and transistor 234 may form the driving circuit for red LED 220.

The anode of IR LED 220 is $V_{IR}$ pin 202, and the cathode of IR LED 220 connects to one side of resistor 222, which limits the current flowing through IR LED 220. The node between IR LED 220 and resistor 222 is $IR_{CATH}$ pin 216, which can be used to bypass the driving circuit in the multifunctional IR module 200 to drive the IR LED 220 externally. For example, it may be beneficial to increase the output intensity of the IR LED 220 past what is possible using the built-in driving circuit of the multifunctional IR module 200. The other side of resistor 222 is connected to the drain of transistor 224. The gate of transistor 224 is $IR_{DRV}$ pin 212. The source of transistor 224 is GND pin 204. The anode of red LED 230 is $V_{RED}$ pin 214, and the cathode of red LED 230 connects to one side of resistor 232, which limits the current flowing through red LED 230. The other side of resistor 232 is connected to the drain of transistor 234. The gate of transistor 234 is $R_{DRV}$ pin 210. The source of transistor 234 is GND pin 204.

A notable characteristic of the multifunctional IR module 200 is that, unlike convention IR modules, it does not include a microcontroller or dedicated application-specific integrated circuit (ASIC). Additionally, unlike many conventional LED applications that rely on current to control LEDs, there is no current conditioning circuit between the PMIC 160 and LED anodes. Instead, the multifunctional IR module 200 uses a voltage output directly from the PMIC 160 to control the current through the LEDs, which makes the overall circuitry much simpler and thus reduces hardware costs. The relationship between changes in voltage from the PMIC 160 and changes in current through the LEDs is non-linear. Using voltage control is particularly useful for heart rate and $SpO_2$ applications because enables control over the intensity of the LEDs without needing a complex circuit. This more easily allows the intensity of the LEDs to vary based factors that affect the intensity of the reflected light, such as skin color and thickness. For example, elderly people generally may have thicker skin than children, so a high intensity is needed for elderly people while a lower intensity is sufficient for children. If the intensity of the reflected light is too high, the signal from the photodiode 240 can become saturated, resulting in a clipped waveform that does not reflect the light being reflected.

Example Multifunctional IR Module Configurations

Various configurations of the multifunctional IR module 200 support a combination of the following features: IR in (receiving IR signals), IR out (generating IR signals), heart rate sensing, $SpO_2$ (oxygen saturation) sensing, distance/proximity detection, gesture detection, LED control, and ambient light detection. IR in is enabled by methods for receiving IR signals described in U.S. Pat. No. 8,983,300, filed on May 6, 2014; U.S. Pat. No. 9,323,710, filed on Feb. 3, 2015; and U.S. patent application Ser. No. 15/085,984, filed on Mar. 30, 2016; all of which are herein incorporated by reference. IR out is enabled by methods for generating IR signals described in U.S. Pat. No. 8,989,583, filed on May 6, 2014, and U.S. Pat. No. 9,342,475, filed on Feb. 3, 2015, both of which are herein also incorporated by reference. The techniques described in the patents and patent application noted above can also be applied to the other features that involve generation or receipt of IR (or red) signals. For example, the multifunctional IR module 200 may be connected to a data bus where signals received from and sent to the PMIC 160 or processor 110 (e.g., signals 161, 163, and/or 164) are associated with a clock signal and an operating frequency based on the clock signal that are ignored by the multifunctional IR module 200. The processor 110 may then transfer a signal that is in the frequency domain (based on the operating frequency) to the multifunctional IR module 200 through the data bus without the operating frequency, generating an IR (or red) signal in the time domain. Similarly, the processor 110 may receive an IR (or red) signal by sampling the analog signal received from the multifunctional IR module based on the operating frequency of the data bus.

The multifunctional IR module 200 measures heart rate by using the photodiode 240 to measure light that is reflected back from either IR LED 220 or red LED 230. Variations of the intensity of the reflected light are indicative of blood pulses. $SpO_2$ is the oxygen saturation of arterial blood as measured by pulse oximetry. Pulse oximetry can be performed by the multifunctional IR module 200 by toggling the IR and red LEDs 220 and 230 at an interval of 5-10 milliseconds and reading the signal output by the photodiode 240. Because oxygenated hemoglobin absorbs more infrared light than red light and deoxygenated hemoglobin absorbs more red light than infrared light, comparison of the level of infrared light reflected and the level of red light reflected results in a $SpO_2$ reading that is expressed as a percentage of oxygenated hemoglobin in the total (oxygenated+deoxygenated) hemoglobin present in the blood. Green light can also be used in lieu of the red light.

Distance/proximity detection involves transmitting an IR signal with multiple embedded frequencies (e.g., 38 khz, 100 khz, and 20 khz). Based on the distance between the multifunctional IR module 200 and an object, multiple reflections change the duty cycle of the IR signal. Distances of 0-15 centimeters can be estimated by comparing the reflected IR signal to the original IR signal. Gesture detection may rely on emitting an IR signal and measuring the variation in the received IR signal. Supported gestures may include taps, and swipes. LED control may refer to the ability to use the LEDs 220 and 230 of the multifunctional module 200 for other purposes. For example, the red LED 230 could be used to indicate the countdown of a camera timer. Additionally, the multifunctional IR module 200 can use the photodiode 240 to measure ambient light, enabling the computing device 100 to determine how it is placed, such as held in a hand, put in a dock, or placed on a table.

Figure 4:
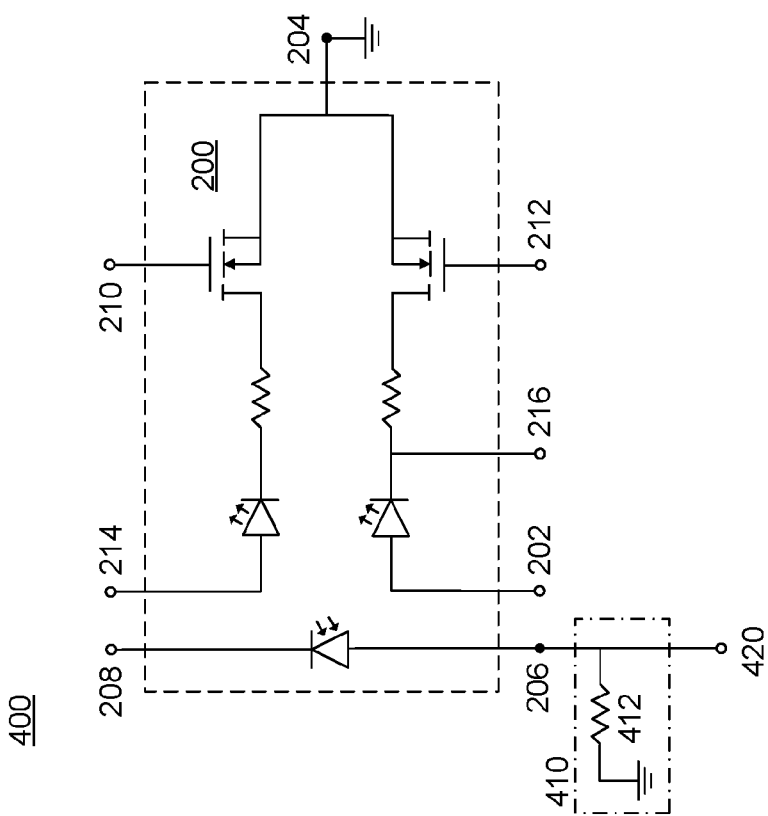

FIG. 4 illustrates an example configuration 400 of the multifunctional IR module 200, according to one embodiment. In configuration 400, the $V_{out}$ signal 420 is (or is derived from, if further described configurations are combined with configuration 400) $PD_{ANOD}$ pin 206 of multifunctional IR module 200. Photodiode 240 is then powered via $PD_{CATH}$ pin 208. Sub-circuit 410 converts the photocurrent of photodiode 240 to voltage. Sub-circuit 410 is connected to $PD_{ANOD}$ pin 206 and includes grounded resistor 412. Resistor 412 can provide gain for the $V_{out}$ signal 420 on the order of 8-10×. The actual gain provided is determined based on the value of resistor 412. Due to the limited gain of configuration 400, it is beneficial to place the multifunctional IR module 200 close in physical proximity to an ADC (i.e., the PMIC 160). Otherwise, the signal received by the photodiode 240 could be drowned out by electrical noise of the computing device 100. Configuration 400 supports generating IR signals, receiving IR signals, and proximity switch functionality. In one embodiment, configuration 400 also includes a unity gain amplifier at $V_{out}$ signal 420 to ensure that it is adequately received by the ADC. This embodiment of configuration 400 is aimed at high electrical noise environments and enables heart rate and $SpO_2$ sensing.

Figure 5:
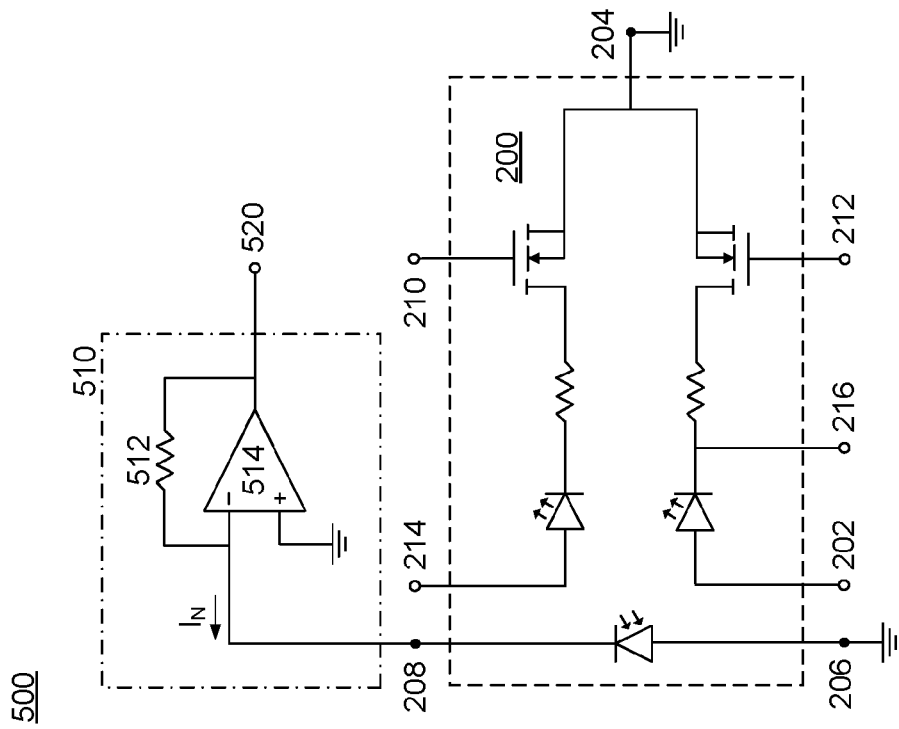
FIGS. 4-7 illustrate example configurations of a multifunctional IR module, according to one embodiment.

FIG. 5 illustrates an example configuration 500 of the multifunctional IR module 200, according to one embodiment. In configuration 500, photodiode 240 is not powered, and $V_{out}$ signal 520 is derived from $PD_{CATH}$ pin 208 of multifunctional IR module 200. Photodiode 240 is not powered because PD$_{CATH}$ pin 208 is used as for the V$_{out}$ signal 520, and PD$_{ANOD}$ pin 206 is connected to ground. Sub-circuit 510 forms an inverting amplifier that includes an op-amp 514 and a resistor 512. In some embodiments, sub-circuit 510 also includes a capacitor in parallel with resistor 512 to smooth out the signal, which leads to better SpO$_2$ sensing. PD$_{CATH}$ pin 208 is connected to resistor 512 and the inverting input of op-amp 514. The non-inverting input of op-amp 514 goes to ground, and the other end of resistor 512 is connected to the output of op-amp 514, which is the V$_{out}$ signal 520. Configuration 500 supports IR in, IR out, heart rate sensing, SpO$_2$ sensing, gesture detection, LED control, and limited distance/proximity detection. Configuration 500 is best suited for SpO$_2$ sensing because V$_{out}$ signal 520 accurately conveys both the AC and DC portions of the reflected signal.

Figure 6:
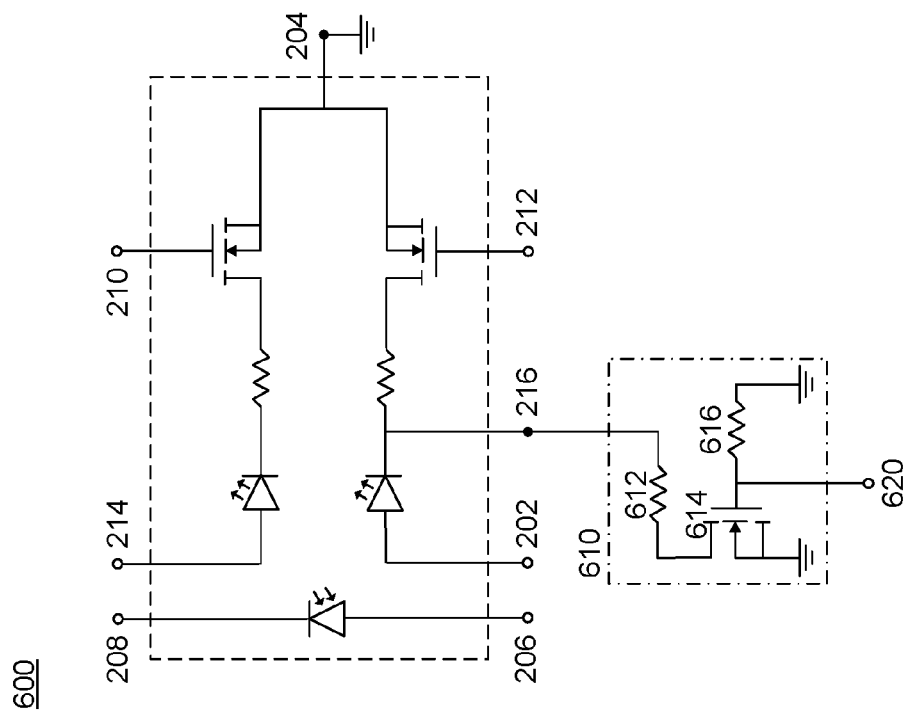

FIG. 6 illustrates another configuration 600 of multifunctional IR module 200 that can be combined with other configurations 400 and 500 of multifunctional IR module 200, according to one embodiment. Configuration 600 uses sub-circuit 610, which functions as a high current driver for IR LED 220. Sub-circuit 610 includes resistors 612 and 616, and transistor 614 (e.g., N-FET). Resistor 612 connects to IR$_{CATH}$ pin 216 on one side and the drain of transistor 614 on the other. The source of transistor 614 is grounded. The gate of transistor 614 is connected to resistor 616, which is also grounded, and IR$_{HIGH}$ pin 620. Sub-circuit 610 generates a high current for IR LED 220 when transistor 614 is turned on via IR$_{HIGH}$ pin 620. Thus, the current of the IR LED 220 can be toggled between high current (when transistor 614 is on), which is optimal for IR communication transmissions and distance sensing, and low current (when transistor 614 is off), which is optimal for sensing heart rate and detecting SpO$_2$.

Figure 7:
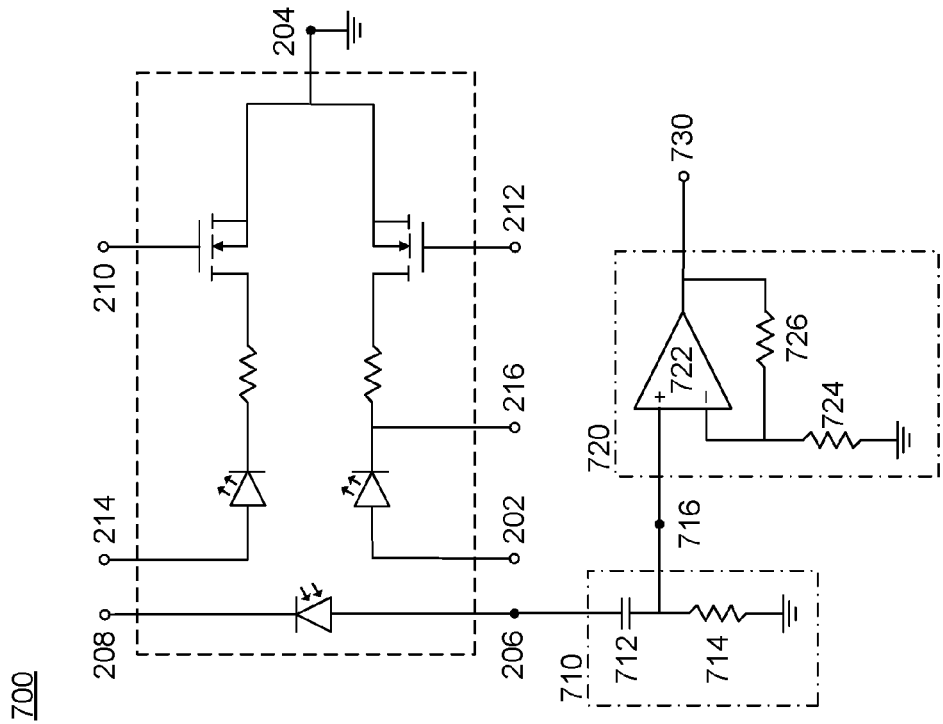

FIG. 7 illustrates an example configuration 700 of the multifunctional IR module 200, according to one embodiment. Configuration 700 can be used on configurations 400 or 500, in addition to configuration 600 in some embodiments. Configuration 700 uses sub-circuit 710, which is a high pass filter, and sub-circuit 720, which is a high gain amplifier. Sub-circuit 710 includes capacitor 712 and resistor 714. Sub-circuit 729 includes op-amp 722, and resistors 724 and 726. PD$_{ANOD}$ pin 206 is connected to capacitor 712 of sub-circuit 710. The other side of capacitor 712 is connected to a grounded resistor 714 and an output 716. Output 716 of sub-circuit 710 connects to the non-inverting input of the op-amp 722 of sub-circuit 720. The inverting input of op-amp 722 is connected to resistors 724 and 726. Resistor 724 is grounded, and resistor 726 connects to the output of op-amp 722, which is the V$_{out}$ signal 730. The combination of sub-circuits 710 and 720 outputs a signal with gain on the order of 1000× via V$_{out}$ signal 730. The gain can be adjusted by modifying resistors 714, 724, and 726.

Configuration 700 removes the DC component from the PD$_{ANOD}$ pin 206 and amplifies the resultant signal. Configuration 700 supports IR in, IR out, heart rate sensing, distance/proximity detection, gesture detection, and LED control. The amplification of the V$_{out}$ signal 730 enables multifunctional IR module 200 to operate even when it is not close in physical proximity to an ADC. Additionally, the amplified V$_{out}$ signal 730 enables easier heart rate sensing over the direct output of PD$_{ANOD}$ pin 206, which is around 20 mV and easily lost en-route to the PMIC 160 due to electrical noise of the computing device 100. Though configuration 700 is shown and described with sub-circuit 710 (and sub-circuit 720, via output 716) connected to PD$_{ANOD}$ pin 206, the high pass filter (sub-circuit 710) and high gain amplifier (sub-circuit 720) can be applied to any pint that is used for output, such as the PD$_{CATH}$ pin 208 in configuration 500. For example, in configuration 500, sub-circuits 710 and 720 can be applied to PD$_{ANOD}$ pin 206 (before sub-circuit 510), or to signal 520 (after sub-circuit 510) in a similar fashion as that described in conjunction with PD$_{ANOD}$ pin 206 above. If sub-circuits 710 and 720 are applied to before sub-circuit 510, the output of the combination of sub-circuits is signal 520. If 710 and 720 are applied to after sub-circuit 510, the output of the combination of sub-circuits is signal 730.

Figure 8:
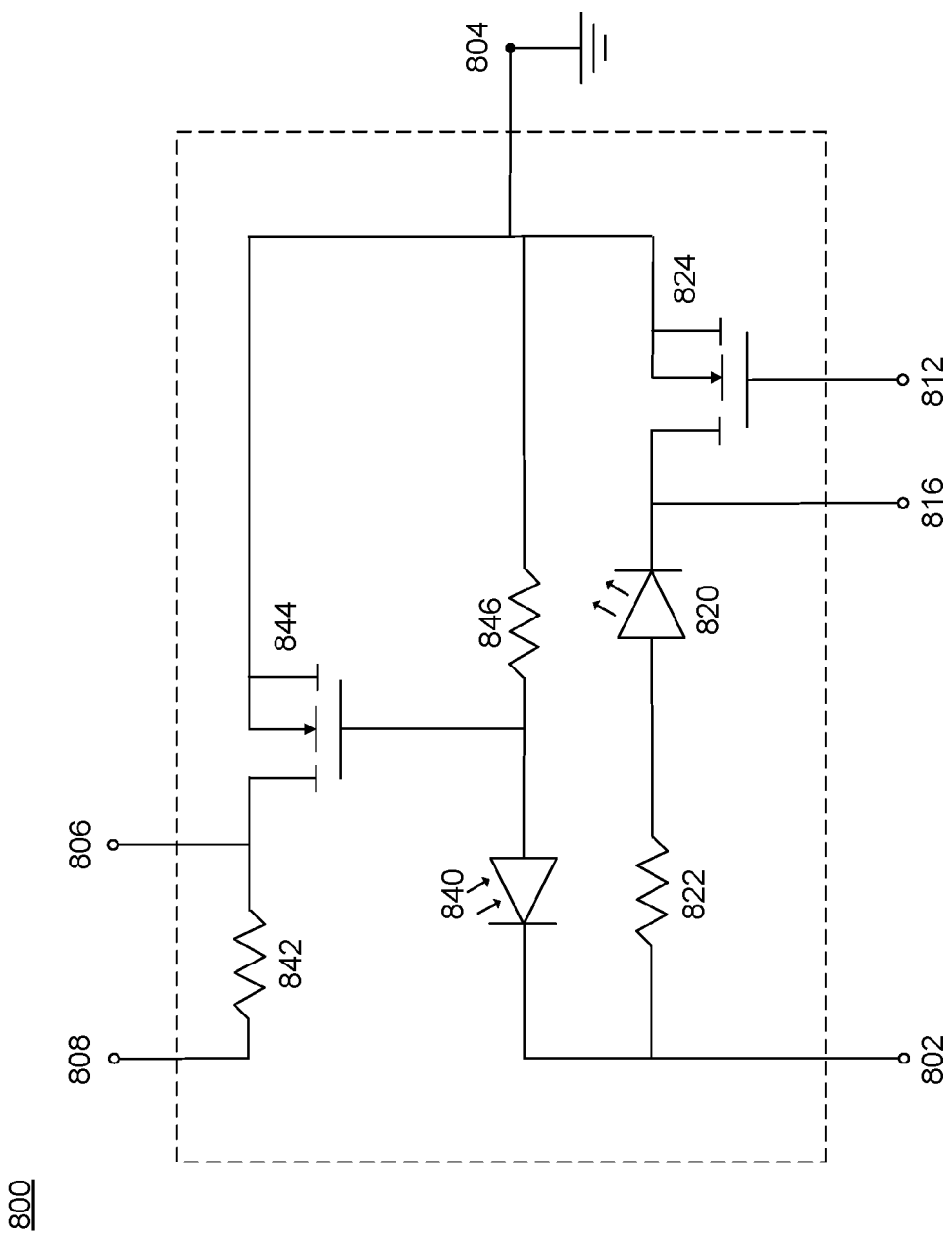
FIG. 8 illustrates circuitry of an IR-only implementation of a multifunctional IR module that receives and outputs digital signals, according to one embodiment.

One skilled in the art will appreciate that only relevant connections are shown and thus the actual connections may vary from those shown in configurations 400-600 of FIGS. 4-6. For example, op-amp power and ground connections are omitted for simplicity, as are capacitors that are used to reduce the noise in the voltage supplies (e.g., those connected to V$_{IR}$ pin 202 and V$_{RED}$ pin 214). Additionally as noted above, configurations 600 and/or 700 can be added to configuration 400 or configuration 500. For example, in one embodiment, Example Digital Embodiment FIG. 8 illustrates circuitry of an IR-only implementation of a multifunctional IR module 800 that receives and outputs digital signals, according to one embodiment. Multifunctional IR module 800 has six pins 802, 804, 806, 808, 812, and 816. V$_{DD-1}$ pin 802 powers the IR LED and the photodiode 840. In some embodiments, V$_{DD-1}$ pin 802 is 3.3 volts or 5 volts. GND pin 804 is the ground. PD$_{out}$ pin 806 is the output of the photodiode 840 as a logic level (i.e., on or off). V$_{DD-2}$ pin 808 provides the on logic level that is used for the output of the photodiode 840. In some embodiments, V$_{DD-2}$ pin 808 is 1.8 volts. IR$_{DRV}$ pin 812 drives the IR LED 820. IR$_{CATH}$ pin 816 is the cathode of the IR LED 820. Multifunctional IR module 800 is shown and described as only having an IR LED 820. However, in some embodiments, multifunctional IR module 800 also has a red LED, which is implemented by adding pins 214 and 210, and circuit components 230, 232, and 234 from multifunctional IR module 200 (replacing ground 204 of multifunctional IR module 200 with ground 804 of multifunctional IR module 800).

The primary components of multifunctional IR module 800 are IR LED 820 and photodiode 840. The circuitry of multifunctional IR module 800 also includes two resistors 822, 842, and 846, and two N-FETs 824 and 844. Resistor 822 and transistor 824 form the driving circuit for IR LED 220. Resistor 822 is connected to V$_{DD-1}$ pin 802 and the anode of IR LED 820. The cathode of IR LED 820 is connected to IR$_{CATH}$ pin 816 and the drain of transistor 824. The source of transistor 824 is grounded, and the gate of transistor 824 is connected to IR$_{DRV}$ pin 812. Transistor 824 works in the same way as transistor 224.

Resistor 842 and transistor 844 form a circuit for converting the photodiode 840 output to a logic level. By connecting the analog output of photodiode 840 to the gate of transistor 844, multifunctional IR module 800 is able to produce a digital (i.e., logic level) output for the PD$_{out}$ pin 806. When the analog output of photodiode 840 is greater than a threshold voltage (e.g., 1 volt), the source and drain of transistor 844 connect and PD$_{out}$ pin 806 is equal to logic high (e.g., equal to V$_{DD-2}$). When the analog output of photodiode 840 is less than the threshold voltage, the source and drain of transistor 844 are disconnected and PD$_{out}$ pin 806 is equal to logic low. The gain of the output of photodiode 840 is controlled by resistor 846 and set high enough such that any IR signal received saturates photodiode 840, making multifunctional IR module 800 particularly suited for applications involving IR in and receiving reflections of IR from a surface (e.g., distance sensing). Multifunctional IR module 800 is unable to measure heart rate or $SpO_2$. However, the lack of op-amp reduces the cost and power consumption of multifunctional IR module 800.

Additional Configuration Considerations

In summary, the disclosed embodiments include a multifunctional IR module comprising an IR light-emitting diode (LED) having an anode and a cathode, a first resistor having a first end connected to the cathode of the IR LED, and a first transistor. A drain of the first transistor is connected to a second end of the first resistor, and a source of the first transistor is grounded. The multifunctional IR module additionally includes an IR receiver having an output. The anode of the IR LED, a gate of the first transistor, and the IR receiver are communicatively coupled to a computing device, and the computing device is configured to receive a signal from the multifunctional IR module based on the output of the IR receiver.

The disclosed example embodiments beneficially allows for a number of functions on a computing device 100. A conventional computing device 100 with signal processing hardware may be able to send and receive signals. However, additional hardware increases the cost of manufacturing mobile devices and increases power consumption within the computing device 100. By using software to perform processing conventionally performed by hardware, the computing device 100 may process infrared signals without additional hardware. Additionally, the disclosed multifunctional IR module 200 combines functionality that is usually separated to minimize the number of hardware components needed. For example, traditionally, IR in and IR out are supported by an IR system with a IR LED and a photodiode, while heart rate sensing and $SpO_2$ sensing are supported by a separate IR LED, red LED and photodiode set-up. The multifunctional IR module 200 combines these separate systems to prevent duplication of components (i.e., IR LED, photodiode, etc.), which further reduces the cost of adding these functionalities to a computing device 100.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. For example, multifunctional IR module 200, multifunctional module 800, and/or any of configurations 400, 500, 600, and 700 (or combination thereof) may be implemented as a single module, a module combined with additional circuit components, or directly on the main circuit board of the computing device. These and other variations, modifications, additions, and improvements fall within the scope of the subject matter herein.

Certain embodiments are described herein as including a number of components, modules, mechanisms, or functionalities, for example, as illustrated in FIGS. 1-10. Modules may constitute either software modules (e.g., code embodied on a machine-readable medium or in a transmission signal) or hardware modules. A hardware module is tangible unit capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

The various operations of example methods described herein may be performed, at least partially, by one or more processors, e.g., processor 110, that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

The one or more processors 110 may also operate to support performance of the relevant operations in a "cloud computing" environment or as a "software as a service" (SaaS). For example, at least some of the operations may be performed by a group of computers (as examples of machines including processors), these operations being accessible via a network (e.g., the Internet) and via one or more appropriate interfaces (e.g., application program interfaces (APIs).)

The performance of certain of the operations may be distributed among the one or more processors 110, not only residing within a single machine, but deployed across a number of machines. In some example embodiments, the one or more processors 110 or processor-implemented modules may be located in a single geographic location (e.g., within a home environment, an office environment, or a server farm). In other example embodiments, the one or more processors 110 or processor-implemented modules may be distributed across a number of geographic locations.

Some portions of this specification are presented in terms of algorithms or symbolic representations of operations on data stored as bits or binary digital signals within a machine memory (e.g., a system memory 120). These algorithms or symbolic representations are examples of techniques used by those of ordinary skill in the data processing arts to convey the substance of their work to others skilled in the art. As used herein, an "algorithm" is a self-consistent sequence of operations or similar processing leading to a desired result. In this context, algorithms and operations involve physical manipulation of physical quantities. Typically, but not necessarily, such quantities may take the form of electrical, magnetic, or optical signals capable of being stored, accessed, transferred, combined, compared, or otherwise manipulated by a machine. It is convenient at times, principally for reasons of common usage, to refer to such signals using words such as "data," "content," "bits," "values," "elements," "symbols," "characters," "terms," "numbers," "numerals," or the like. These words, however, are merely convenient labels and are to be associated with appropriate physical quantities.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories 120 (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the invention. This description should be read to include one or at least one and the singular also includes the plural unless it is obvious that it is meant otherwise.

Upon reading this disclosure, those of skill in the art will appreciate still additional alternative structural and functional designs for a multifunctional IR module through the disclosed principles herein. Thus, while particular embodiments and applications have been illustrated and described, it is to be understood that the disclosed embodiments are not limited to the precise construction and components disclosed herein. Various modifications, changes and variations, which will be apparent to those skilled in the art, may be made in the arrangement, operation and details of the method and apparatus disclosed herein.

What is claimed is:

1. A multifunctional infrared (IR) module comprising:
    an IR light-emitting diode (LED) having an anode and a cathode;
    a first resistor having a first end connected to the cathode of the IR LED;
    a first transistor, wherein a drain of the first transistor is connected to a second end of the first resistor, and a source of the first transistor is grounded;
    an IR receiver having an output, and
    a high current driving circuit connected to the cathode of the IR LED, the high current driving circuit comprising:
        a second resistor connected with a first end connected to the cathode of the IR LED, and
        a second transistor, a drain of the second transistor connected to a second end of the second resistor, and a source of the second transistor connected to ground,
    wherein the anode of the IR LED, a gate of the first transistor, and the IR receiver are communicatively coupled to a computing device, and the computing device is configured to receive a signal from the multifunctional IR module based on the output of the IR receiver,
    wherein a signal applied to the gate of the second transistor increases the current of the IR LED.

2. The multifunctional IR module of claim 1, wherein the IR receiver is a photodiode.

3. The multifunctional IR module of claim 2, wherein the output of the photodiode is an anode of the photodiode.

4. The multifunctional IR module of claim 2, wherein the output of the photodiode is a cathode of the photodiode.

5. The multifunctional IR module of claim 2, wherein the photodiode is not powered.

6. The multifunctional IR module of claim 1, wherein the IR receiver is a phototransistor.

7. The multifunctional IR module of claim 1, further comprising:
    a second resistor with a first end connected to the output of the IR receiver and a second end connected to ground.

8. The multifunctional IR module of claim 7, further comprising:
    a unity gain amplifier connected to the output of the IR receiver.

9. The multifunctional IR module of claim 8, further comprising:
    an inverting amplifier connected to the output of the IR receiver,
    wherein the signal received by the computing device is the output of the inverting amplifier.

10. The multifunctional IR module of claim 9, wherein the IR receiver is a photodiode having a cathode and an anode, the output of the IR receiver being from the cathode of the photodiode, the anode of the photodiode connected to ground.

11. The multifunctional IR module of claim 1, wherein the multifunctional IR module is additionally configured to send IR communication transmissions, and wherein an intensity of the IR LED when sending IR communication transmissions is greater than an intensity of the IR LED when measuring heart rate.

12. The multifunctional IR module of claim 1, wherein the signal from the IR receiver is filtered to remove a direct current (DC) component of the signal before being received by the computing device.

13. The multifunctional IR module of claim 12, further comprising:
    a high pass filter connected to an output of the IR receiver; and a high gain amplifier connected to an output of the high pass filter, wherein the signal received by the computing device is the output of the high gain amplifier.

14. The multifunctional IR module of claim 1, wherein the signal received by the computing device from the IR receiver includes both DC and alternating current (AC) components.

15. The multifunctional IR module of claim 1, further comprising:

a red LED having an anode and a cathode;

a second resistor connected to the cathode of the red LED; and a second transistor, wherein a drain of the second transistor is connected to the second resistor, and a source of the second transistor is grounded, wherein the anode of the red LED, and a gate of the second transistor are communicatively coupled with the computing device.

16. The multifunctional IR module of claim 15, wherein the multifunctional IR module is configured to measure $SpO_2$.

17. The multifunctional IR module of claim 1, wherein the multifunctional IR module is configured to measure heart rate.

* * * * *